(12) United States Patent
Smeets et al.

(10) Patent No.: US 8,604,188 B2
(45) Date of Patent: Dec. 10, 2013

(54) WASHING OF AN ORGANIC PHASE COMPRISING CAPROLACTAM

(75) Inventors: Theodorus Maria Smeets, Elsloo (NL); Leonardus Joseph Raets, Elsloo (NL); Cornelis Marinus Van Liujk, Geleen (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 13/060,885

(22) PCT Filed: Sep. 2, 2009

(86) PCT No.: PCT/EP2009/061307
§ 371 (c)(1),
(2), (4) Date: May 23, 2011

(87) PCT Pub. No.: WO2010/026147
PCT Pub. Date: Mar. 11, 2010

(65) Prior Publication Data
US 2011/0224428 A1      Sep. 15, 2011

(30) Foreign Application Priority Data
Sep. 4, 2008 (EP) .................................. 08015595

(51) Int. Cl.
*C07D 201/16*   (2006.01)
(52) U.S. Cl.
USPC ........................................................ 540/540
(58) Field of Classification Search
USPC ........................................................ 540/540
See application file for complete search history.

(56) References Cited

U.S. PATENT DOCUMENTS 6,849,731 B2 * 2/2005 Dsinter-De Hondt et al. ............................ 540/540

FOREIGN PATENT DOCUMENTS

| GB | 1 175 659 | 12/1969 |
| WO | 99/65873 | 12/1999 |
| WO | 02/070475 | 9/2002 |

OTHER PUBLICATIONS

International Search Report for PCT/EP2009/061307, mailed Oct. 15, 2009.
Written Opinion for PCT/EP2009/061307, mailed Oct. 15, 2009.
Database Caplus [online], Chemical Abstracts Service, Columbus, Ohio, US; Liu et al.; "Recovery of Caprolactam from Waste Water in Caprolactam Production using Pulsed-sieve Plate Extraction Column", XP002514478, (2002).
Zuiderweg "Sieve Trays a View on the State of the Art", Chemical Engineering Science, Oxford, GB, vol. 37, No. 10, Jan. 1, 1982, pp. 1441-1464, XP009062628.
CN Official Action and Search Report, CN Appln. No. 200980134738.4 (Sep. 27, 2012).

* cited by examiner

*Primary Examiner* — Bruck Kifle
(74) *Attorney, Agent, or Firm* — Nixon & Vanderhye P.C.

(57) ABSTRACT

The invention relates to a process for extracting an impurity from an organic phase comprising caprolactam, comprising extracting the impurity by washing said organic phase as a discontinuous phase with an aqueous phase as a continuous phase, the ratio of the flow of the aqueous phase in $m^3/hr$, to the flow of the organic phase in $m^3/hr$, being 0.05 or less. Further the invention relates to a caprolactam production plant, wherein use can be made of a process of the invention.

12 Claims, 4 Drawing Sheets

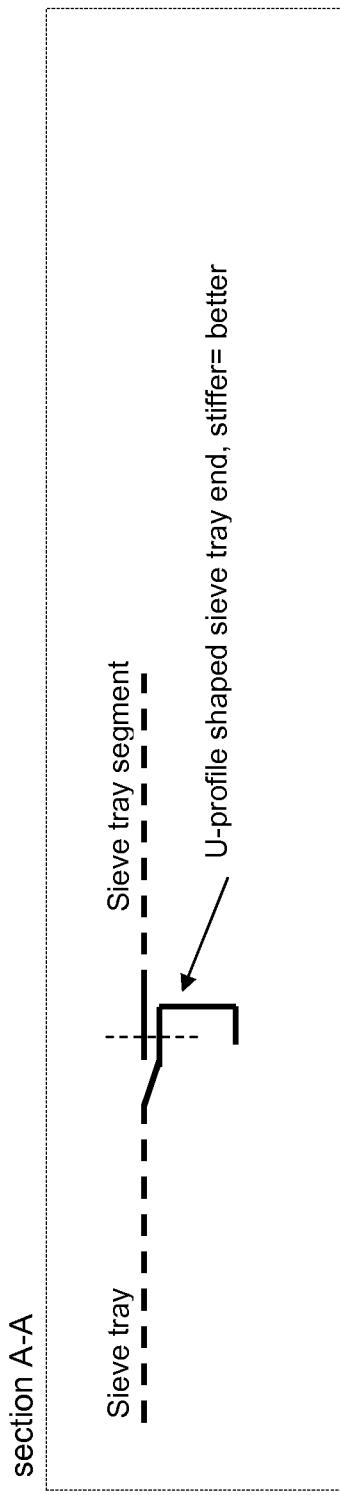

WASHING OF AN ORGANIC PHASE COMPRISING CAPROLACTAM

This application is the U.S. national phase of International Application No. PCT/EP2009/061307, filed 2 Sep. 2009, which designated the U.S. and claims priority to European Application No. 08015595.5, filed 4 Sep. 2008, the entire contents of each of which are hereby incorporated by reference.

The invention relates to a process for extracting an impurity from an organic phase comprising caprolactam. The invention further relates to a caprolactam plant using a specific washing column for removing an impurity from a stream in the plant.

WO 2002/070475 describes a process for wherein caprolactam is recovered from a solution comprising caprolactam dissolved in an organic solvent, said process comprising: a) washing the solution with water or an aqueous alkaline solution, resulting in a washed solution comprising caprolactam and organic solvent and in a washing residue, b) evaporating organic solvent from the washed solution, resulting in caprolactam product, c) optionally, hydrogenating the caprolactam product, d) optionally, evaporating water from the caprolactam product, e) distilling the caprolactam product to recover caprolactam and a distillation residue, f) extracting the distillation residue with an organic solvent in the presence of water to obtain (i) an extract comprising caprolactam dissolved in organic solvent and (ii) an aqueous effluent, and g) recycling the extract to step a) or b).

In WO 2002/070475 only a packed column, namely a pulsed packed column, is mentioned as equipment for washing the caprolactam in organic solvent.

The use of a packed column has been found disadvantageous in that it has been experienced that a substantial amount of sulphur-containing impurity may be retained in the treated product, comprising caprolactam. Accordingly, washing performance is insufficient, especially when applied in columns of large diameters. This malfunction is, in the opinion of the present inventors, clearly related to the choice of hydrodynamic concept in WO 2002/070475 in combination with the extremely low feed ratio used, which ratio is (or in fact needs to be) applied in order to avoid substantial loss of caprolactam via the washing liquid and/or laborious additional steps for recovering such lost amounts of caprolactam from the washing liquid. Feed ratio as mentioned here is the ratio of the amount ($m^3/h$) of washing liquid, generally (alkalinic) water fed to the column and of the amount ($m^3/h$) of organic phase to be washed.

It is thus an object of the present invention to provide a novel process for extracting an impurity from an organic phase comprising caprolactam.

It is in particular an object of the invention to provide such a process wherein the loss of caprolactam from the organic phase, as a result of the extraction, is small.

It is in particular an object of the invention to provide a process for extracting an impurity, especially an impurity comprising a sulphur-containing compound, from an organic phase comprising requiring little water.

It is in particular a further object of the invention to provide a process that is able to provide excellent washing performance no matter to what size the commercial scale column is scaled up to.

Moreover, it is also an object of the invention to provide a process for extracting an impurity from an organic phase comprising caprolactam which can be carried out using equipment that requires little maintenance.

The present invention accordingly specifically aims at solving the problem of simultaneously being able to use very low feed ratio of washing liquid while still achieving high washing performance in extracting an impurity from an organic phase comprising caprolactam.

One or more objects that may be met in accordance with the invention will become apparent from the description and/or claims herein below.

It has now been found that one or more objects underlying the invention are met by extracting an impurity, in particular a sulphur-containing compound, from an organic phase comprising caprolactam, using an aqueous phase in a specific way.

Accordingly, the present invention relates to a process for extracting an impurity from an organic phase comprising caprolactam, comprising extracting the impurity by washing said organic phase as a discontinuous phase with an aqueous phase as a continuous phase, the ratio of the flow of the aqueous phase in $m^3/hr$ to the flow of the organic phase in $m^3/hr$, being 0.05 or less.

The washing liquid generally used is water or alkalinic water which has higher potential to absorb caprolactam. The amount of (preferably alkalinic) water that may be used in the washing step should preferably be very low in order to prevent large amounts of caprolactam to be lost in the discharged wash water or to be reclaimed again from the discharged wash water. The ratio of the amount of (preferably alkalinic) water fed to the column and of the amount of organic phase to be washed is hereinafter referred to as the feed ratio, a term also commonly used by the skilled man. In a commercial plant this ratio according to the present invention now can be lowered so as to be even as low as 0.01 which is far beyond common ranges until the priority date known to or expected to be achievable by the expert in the Liquid-Liquid extraction field while still achieving excellent removal of impurities. The difficulty generally caused by such low feed ratio is the consequence that inside the columns according to the state of art this is reflected as a low phase ratio in the same order of magnitude as the feed ratio. The term phase ratio as used herein reflects the actual ratio of aqueous phase and organic phase inside the column. Without the special provisions required by the present invention, this phase ratio would be close to the feed ratio which is as said extremely low in this particular case for washing of organic phase comprising caprolactam. The present invention aims at solving the problem of simultaneously being able to use very low feed ratio of washing liquid while still achieving high washing performance in extracting an impurity from an organic phase comprising caprolactam.

The inventors believe that the essential difference between the column of the invention and those used in the prior art processes is due to the fact that hold-up in the column is substantially increased as compared with the prior art conditions. It is to be noted, that the column as described in WO 2002/070475 indeed has no provisions to drastically increase the hold-up of the wash liquid inside the column. The hold-up is the fraction of available column volume that is taken by the wash liquid. In the column of WO 2002/070475 this hold-up will be close to the feed ratio of 0.01 (in WO 2002/070475 this ratio is said to be 0.001-0.05)), which the skilled man until now always considered to be too low in view of the required efficiency of the washing operation. The washing liquid in WO 2002/070475 is therefore present in the column as a dispersed phase, i.e. it is distributed as droplets passing downwardly through the column. This aqueous phase in WO 2002/070475 may also be called the discontinuous phase while the organic phase therein can be referred to as continuous phase.

Further until now, it was believed to be principally impossible to achieve an even distribution of the small water flow (in this case of 1 m³/hr) over a large column area (diameter >2 m) while ensuring as well droplets formation of the right size. Beyond this difficulty it was considered by the skilled man at the priority date of the present invention that such a dispersion of droplets, even when created satisfactorily at the inlet position (feed into the column) of the washing liquid, can not be maintained over the entire packing height of the column without substantial maldistribution taking place. Further, the use of a pulsed packed column makes the installation relatively complicated and relatively maintenance-intensive (as a pulse generator is needed).

Thus in the hydrodynamic concept of the invention the organic phase is the dispersed phase in the column, which is distributed in the form of droplets passing through the (alkalinic) aqueous phase which aqueous phase is the continuous phase in the present invention.

Further, the invention relates to a caprolactam production plant comprising a reaction zone for producing caprolactam, downstream of said reaction zone a neutralisation zone for neutralising the caprolactam stream leaving said reaction zone, downstream of the neutralisation zone a first extraction zone for extracting caprolactam from the neutralised caprolactam stream into an organic phase, and downstream of the first extraction zone a second extraction zone for washing the organic phase comprising caprolactam with an aqueous phase, the second extraction zone comprising a sieve tray type wash column equipped with downcomers, in which column the aqueous phase is present as the continuous phase and the organic phase is present is present as the dispersed phase.

Further, the invention relates to the use of a sieve tray type wash column equipped with downcomers for removing one or more sulphur-containing compounds from a organic phase comprising caprolactam.

The invention surprisingly allows a satisfactory or even improved removal of an impurity, also at a low feed ratio, such as a ratio of 0.05 or less. Besides the advantage that thus little water is needed, this has been found advantageous to reduce loss of caprolactam out of the organic phase, thus providing a purified organic phase comprising a high concentration of caprolactam.

Further, in a process of the invention the entrainment of water can be avoided or at least be kept at such a low level that substantial problems as a result of entrainment are avoided or at least ameliorated.

The impurity may include one or more substances selected from the group of salts, coloured compounds and organic acids.

A process according to the invention may in particular be used to extract one or more inorganic sulphur-containing compounds (such as sulphates, sulphites). In particular, sulphate may be present as a result of a neutralisation step of the caprolactam stream. The sulphate concentration of the organic phase prior to extraction in accordance with the invention may for instance by about 50 ppm (by weight, measured as sulphate) or more, in particular about 100 ppm or more. A sulphate concentration below about 5 ppm is desirable, in particular in order to avoid undesired fouling in the further processing of the organic phase comprising caprolactam.

By extraction in accordance with the invention, it has been found possible to remove inorganic sulphur-containing compounds to obtain an organic phase containing less than 5 ppm total inorganic sulphur-containing compounds (by weight measures as the compounds), less than 3 ppm total inorganic sulphur-containing compounds, or even 1 ppm or less of total inorganic sulphur-containing compounds. In particular, the sulphate concentration may be less than 3 ppm or even less than 1 ppm.

The inventors have further found that one or more organic sulphur-containing compounds may be present in an organic phase comprising caprolactam. Examples of such organic compounds are sulphonic acids. The total concentration of organic sulphur-containing compounds in the organic phase prior to extraction may be over 10 ppm (by weight, measured as elemental sulphur), e.g. about 50 ppm or more. The presence of an excessive amount of organic sulphur-containing compounds is undesired because they may lead to problems further downstream in the processing of the organic phase, e.g. in the further purification of the caprolactam. For instance, it is thought that they may cause fouling and/or adversely interfere with the purification efficiency.

In a process according to the invention is suitable to remove organic sulphur adequately, if desired. For instance, it is feasible to obtain an organic phase comprising less than 10 ppm, or even less than 5 ppm, total organic sulphur-containing compounds, e.g. starting from an organic phase comprising several tens ppm of organic sulphur.

It is in particular surprising that such effective removal is feasible whilst the loss of caprolactam from the organic phase is small.

Figure 1:
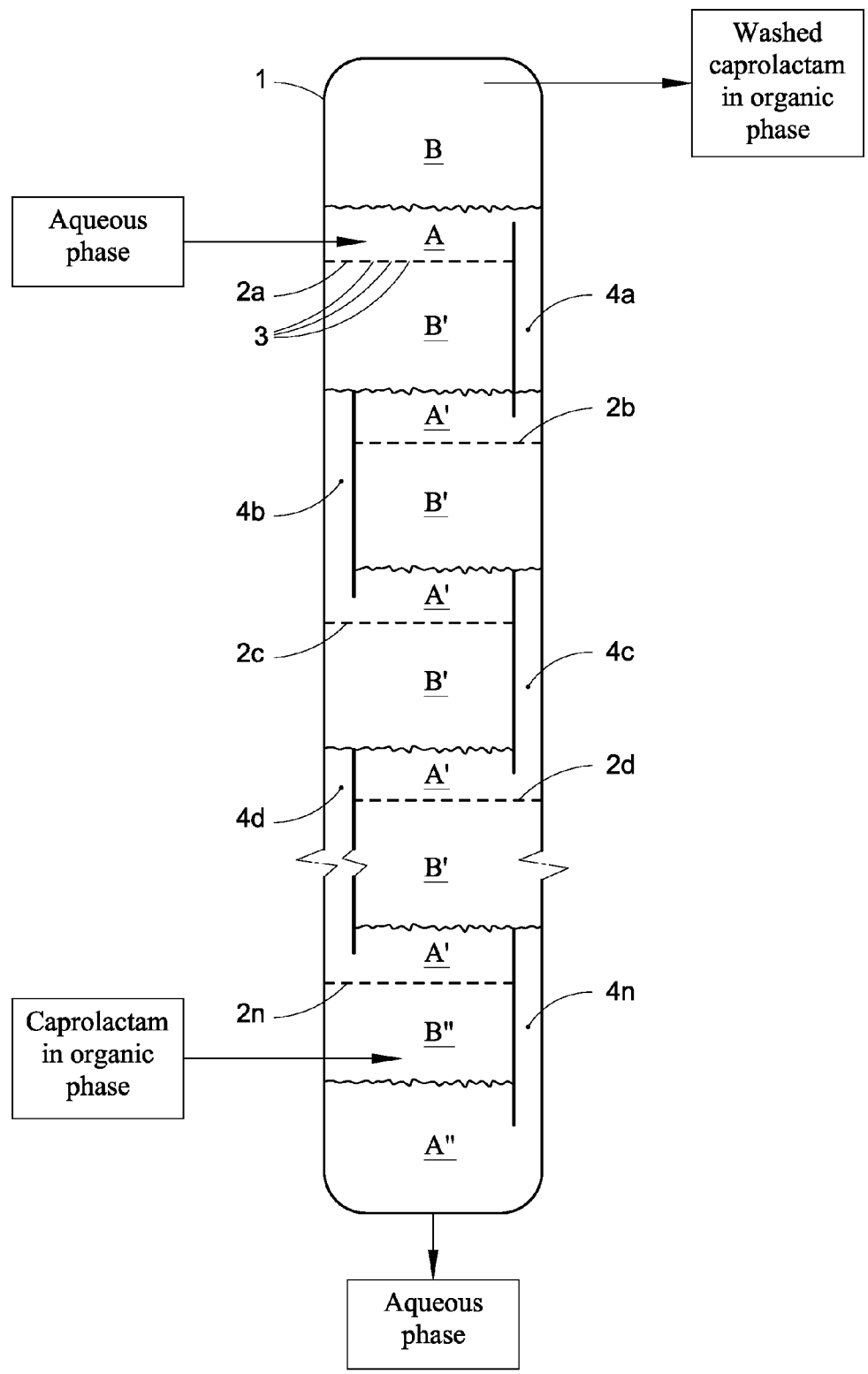
FIG. 1 shows a sieve-tray type wash column, which may be used in a process of the invention or present in a plant of the invention. For details regarding FIG. 1 reference is made to the separate discussion of this Figure hereinbelow.

The term "or" as used herein means "and/or" unless specified other wise.

The term "a" or "an" as used herein means "at least one" unless specified other wise.

When referring to 'ppm', a concentration expressed as parts per million based on weight is meant. For inorganic sulphur-containing compounds, the value is based on the weight of the total compound (or ion, such as sulphate, (in case of a salt)). The concentration may be determined by chromatography, in particular by ion exchange chromatography for ionic species (such as sulphate). For organic sulphur-containing compounds the concentration is based on the weight of elemental sulphur in the compounds, as may be determined by element analysis, and taking into account correction for sulphur-ion concentrations as detected by ion-chromatography.

When referring to a 'noun' (e.g. a compound, an additive etc.) in singular, the plural is meant to be included, unless specified otherwise.

The inventors have realised that it is possible to wash the organic phase with an aqueous phase to remove an impurity, using water or an aqueous solution as the continuous phase and the organic phase as the discontinuous phase without requiring a large amount of water. They found that this can be done by choosing conditions which result in a substantial hold-up of the aqueous phase in an extraction unit wherein the extraction is carried out. The extraction may in particular be carried out in an extraction unit wherein the hold-up is at least 0.2, in particular at least 0.4, more in particular at least 0.45. Usually the hold-up is 0.9 or less, in particular 0.75 or less, more in particular 0.6 or less.

The inventors further surprisingly found that it is possible to carry out a process of the invention using a low feed ratio (as defined earlier: feed rate of water or alkalinic water in m³/hr to the feed rate of organic phase in m³/hr) in an embodiment wherein the hold-up is as high as indicated above. In particular, it has been found possible to carry out a process of the invention in a continuous process, wherein the feed ratio is 0.05 or less, whilst the hold-up in the extraction unit is considerably higher, for instance at least about 0.2 or at least about 0.4.

To avoid a high loss of caprolactam and for a low water usage the feed ratio is 0.05 or less, in particular 0.04 or less, preferably 0.03 or less, more preferably 0.02 or less. In particular, good results have been obtained in a process wherein the feed ratio is about 0.01. The feed ratio is usually at least 0.001, in particular at least 0.002, more in particular at least 0.004.

In particular, good results have been achieved with a process, wherein repeatedly the organic phase is first dispersed in the aqueous phase and thereafter droplets of the organic phase (dispersed in the aqueous phase) are allowed to coalesce. Such dispersing and coalescing may be repeated as often as desired, usually at least 4 times, preferably at least 6 times or at least 8 times. Usually the dispersing and coalescing is repeated 15 times or less, in particular 12 times or less.

In a preferred embodiment of the invention use is made of a sieve tray type wash column equipped with downcomers. Such column may in particular be used to repeatedly form a dispersion of organic phase droplets in aqueous phase and allowing said droplets to coalesce. A sieve tray type wash column has been found particularly suitable to remove an impurity from the organic phase, in particular to remove one or more inorganic sulphur-containing compounds and/or one or more organic sulphur-containing compounds. Such column has further been found especially advantageous in that it requires a little amount of water per volume of treated organic phase. Further, a process comprising the use of such column is robust in that the risk of unacceptable flooding in the column (movement of organic phase droplets in the aqueous phase against the general flow direction of the organic phase) is low. Further, the operation of the column is relatively maintenance friendly compared to a pulsed packed column. Further, a relatively small column may be sufficient for a satisfactory result.

Sieve tray wash columns are trayed columns comprising a number of sieve trays located above each other. The trays comprise a plurality of holes, through which the organic phase flows during use.

In a preferred method of the invention the organic phase is jetted through the holes. This is advantageous for dispersing the organic phase in the aqueous phase.

The velocity at which organic phase is jetted into aqueous phase (through holes in the trays) influences the average size of droplets of organic phase dispersed in aqueous phase. In general, the higher the velocity, the smaller the average droplet size and the quicker an impurity may be removed from the droplet, but also the longer it may take for the droplets to coalesce again. Usually, the velocity of organic phase flowing into aqueous phase is over 20 cm/sec, in particular 30 cm/sec or more. In an advantageous embodiment of the invention, organic phase is jetted into aqueous phase at a velocity of at least 40 cm/sec, in particular of at least 50 cm/sec. In an advantageous embodiment of the invention, organic phase is jetted into aqueous phase at a velocity of 80 cm/sec or less, in particular of 70 cm/sec or less.

Sieve tray wash columns are generally known in the art. FIG. 1 schematically shows a sieve tray wash column 1. Herein an organic phase is washed that has a lower specific weight than the aqueous phase. Herein, the aqueous phase is fed into the column 1 above the top tray 2a, wherein organic phase is forced through the holes 3 in the top tray 2a and mixed with the aqueous phase forming a layer A of a mixture of organic phase in aqueous phase. On top of this mixed layer A a layer B of washed organic phase (comprising caprolactam) is formed which leaves the column at the outlet situated above the inlet for aqueous phase. Aqueous phase moves downstream towards the next tray 2b (below the top tray) via downcomer 4a. The downcomer is preferably designed so as to ensure that its lower end is sufficiently dipped into the aqueous phase of tray 2b. This prevents any short-cutting of the organic phase through the downcomer. Usually therefore no substantial amounts of dispersed organic phase stream downwardly through the downcomer. As an additional precaution also baffles may be fitted around the downcomer. Avoiding net-downstream movement of organic phase is achieved by a sufficiently low down-flow velocity (<0.3 mm/sec) of aqueous phase (allowing upward movement of the organic phase droplets). This is generally achieved as a result of the low water flow rate relative to the organic phase flow rate in a process of the invention. Further, the higher the diameter of the downcomers, the lower the downstream velocity (in cm/sec), will be, under otherwise the same conditions.

The aqueous phase leaving downcomer 4a is mixed with organic phase forced through holes in tray 2b.

This process takes place above each tray (2c, 2d, ... 2n), the space between two trays each forming an extraction zone wherein droplets of organic phase become dispersed in an aqueous phase forming a layer A' and are allowed to coalesce again to form an organic layer B' on top of the layer A'.

Below the lowest tray 2n, aqueous phase used for the extraction (comprising impurity) typically forms a layer A" at the bottom of the column 1. The aqueous phase A" typically leaves the column via an outlet situated in or close to the bottom of the column 1. This allows organic phase dispersed in the aqueous phase to coalesce (and flow upward as it has a lower specific weight than water). Organic phase (comprising caprolactam and impurity) is usually introduced into the column at a level above the aqueous layer A" at the bottom and below the lowest tray, forming a layer B".

As will be understood by the skilled person, in case the organic phase has a higher specific weight than the aqueous phase, a sieve tray wash column may be used wherein the aqueous phase is usually fed via the bottom, and the organic phase via the top.

Usually, the sieve tray wash column comprises at least 4 perforated trays (sieve trays). If desired, a larger number of trays may be present. In general, the larger the number of trays, the more complete the removal of one or more impurities, under otherwise the same conditions. On the other hand, the larger the number of trays, the higher the column or the smaller the distance between trays will be. For an advantageous impurity removal, the number of trays preferably is at least 6 or at least 8. Especially for removal of an impurity in the form of organic sulphur-containing compound(s) from an organic phase comprising caprolactam down to a very low level (e.g. of about 1 ppm or less), it may be advantageous to provide a column with at least 10 trays. The upper limit is not critical. Taking into consideration the height of the column, the number of trays is usually 15 or less, in particular 12 or less.

The perforation geometry of each of the trays is not very critical, but determines the size of the droplets and of an even distribution of the droplets over whole the water phase area on that tray. The diameter of the holes is suitably at least 1 mm. In principle the diameter may be less, but the smaller the holes, the higher the risk of clogging. Taking into account that it is desired to jet the organic phase through the holes of a tray into aqueous phase (situated on said tray), the diameter of the holes preferably is 3 mm or less. The pitch of the holes is at least 15 mm, but usually no larger than 40 mm, preferably 25 mm. Further, as known to the skilled person, the thickness of the tray sheet metal chosen for mechanical reasons also influences the droplets formation, and also the technique used for perforating the sheet like drilling punching or lasering may have some effect on droplets formation. Moreover, the tightness of the tray assembly, will usually influence available pressure drop needed for jetting. Each tray is preferably provided with blind sections at the wall side as calming zones (see FIG. 2A) to allow for control of the overall water circulation on a tray. This movement of the water phase also may propagate to the coalescing organic layer on top of the water layer. For this reason the trays are preferably fitted with baffles (wave breakers) at their bottom side.

Figure 2A:
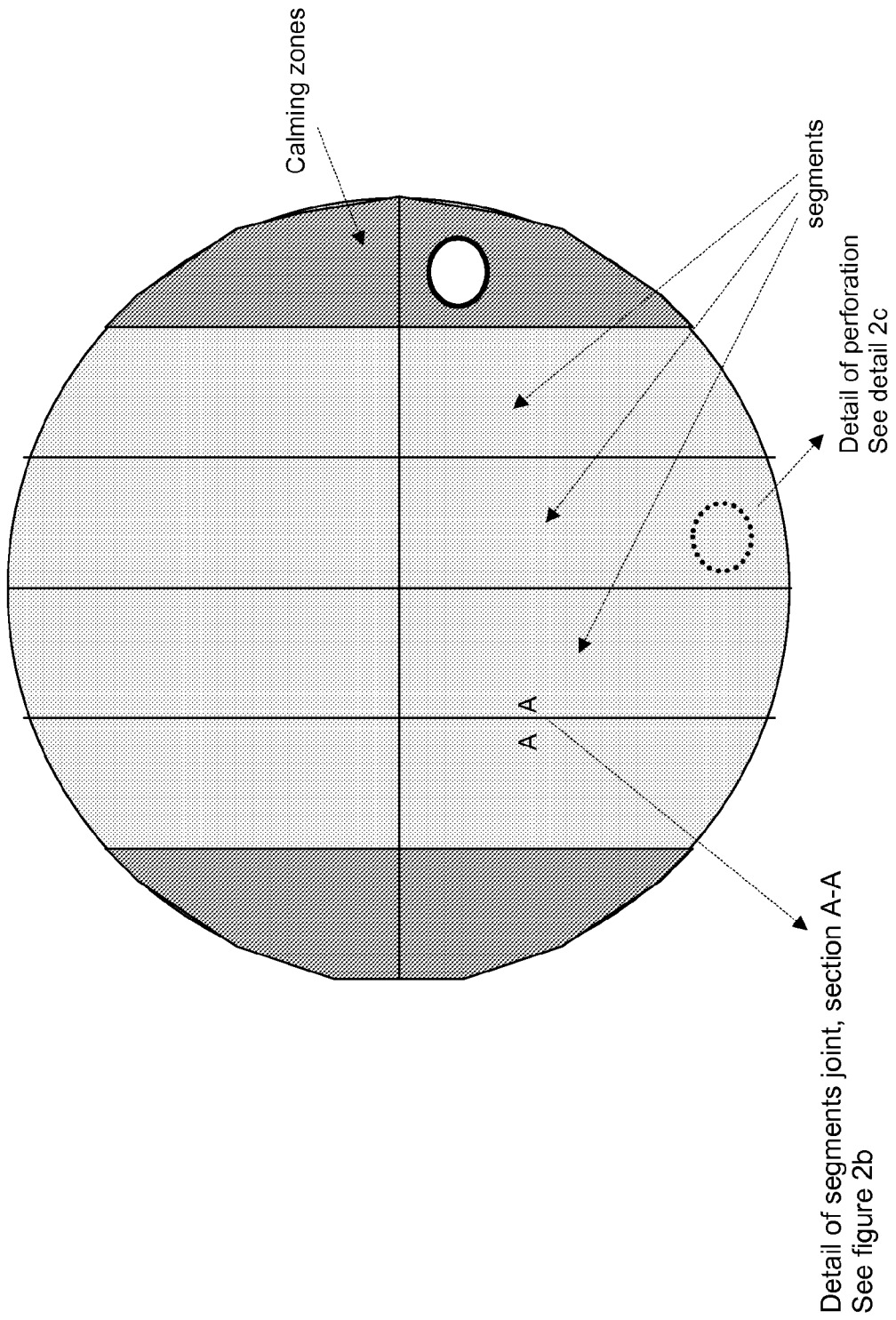
FIG. 2 shows respectively in 2A a schematical view of a cross section of a sieve tray as used, with segments, downcomer and calming zones; in 2B a detail of a joint of segments of the sieve tray, as indicated by section A-A; in 2C a detail of the perforation of the sieve tray segments.
Figure 2C:
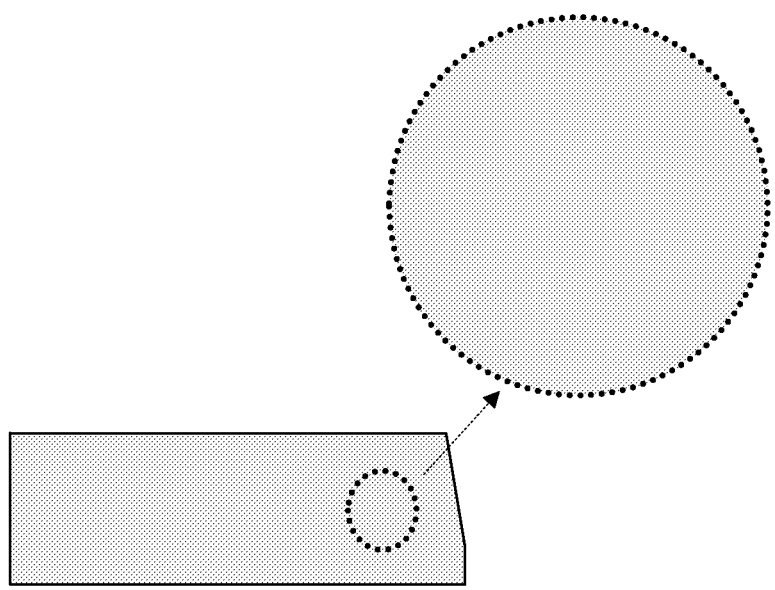

In a plant scale column the trays are most suitably assembled from tray segments, linked together by means of joints (see section A-A in FIG. 2B). This assembly preferably also uses some additional measures for achieving sufficient mechanical strength and stiffness. Both demands, mechanical strength and wave breaking, are preferably combined by choosing the appropriate shape of the tray segments. The overlapping edges of the segments are most preferably U shaped (horizontal U shape) at their bottom side. In FIGS. 2A-2C a schematic drawing of a sectional sieve tray and the way of joining the segments provided with wave breakers are displayed.

The distance between subsequent trays can be chosen within wide limits. In practice, the distance is usually at least 0.5 m. A relatively large distance, such as a distance of at least 0.6 m, and in particular of at least 0.65 m is advantageous in that it helps to compensate for an adverse effect of a possible temporary variation of the flow of the organic phase into the column. On the other hand, the larger the distance, the higher the column needs to be for a given number of trays. In view thereof, the distance between trays is usually 1.0 or less, in particular 0.8 m or less or about 0.75 m or less.

The organic phase comprising caprolactam usually comprises at least one solvent selected from the group of aromatic hydrocarbons, halogenated hydrocarbons $C_4$-$C_{10}$ aliphatic alcohols and $C_4$-$C_{10}$ cycloaliphatic alcohol. Examples are benzene, toluene, chloroform, cyclohexane, decahydronaphtalene, trichloroethane and 4-methyl-2-pentanol, including mixtures thereof. Benzene is a preferred solvent because impurities, such as inorganic and/or organic sulphur-containing compounds, can be efficiently be extracted from benzene using very little water. Toluene is a preferred solvent for its low toxicity. Further, toluene is in particular useful for avoiding substantial problems related to entrainment of water in the organic phase.

The organic phase treated in a process of the invention may in particular be a stream formed in a process for preparing caprolactam via a Beckmann rearrangement. Such processes are generally known in the art, e.g. from Ullmann's encyclopedia of Industrial Chemistry, for instance the $7^{th}$ edition (2005).

The concentration of caprolactam in the organic phase may be a concentration as is provided by a production process, known per se.

In particular, caprolactam may be present in a concentration of a least 15 wt. % caprolactam, more in particular at least 22 wt. % caprolactam (relative to the total organic phase). The caprolactam concentration usually is less than 35 wt. % caprolactam, in particular 30 wt. % or less caprolactam, more in particular 28 wt. % or less caprolactam.

The aqueous phase to be used for extraction is water or an aqueous liquid comprising water as the major component, i.e. a liquid wherein the water content is more than 50 wt. %, based on total weight. Usually, the water content of the aqueous phase is at least 95 wt. %, in particular at least 98 wt. %. The upper limit is determined by the optional presence of one or more additional components. The water content may in particular be up to 100 wt. % or, if an additional component is present, 99.5 wt. % or less or 99 wt. % or less. In addition to water, one or more additives, such as one or more other solvents and/or pH-modifiers, may be present which may help to increase the affinity of the impurity for the aqueous phase. Such additive is preferably chosen such that the affinity of caprolactam for the aqueous phase is not increased or at least increased to a lesser extent.

In particular for removal of an impurity from an organic phase comprising caprolactam, it is advantageous that the pH of the aqueous phase is alkaline. Thus, in such embodiment preferably a base is present in the aqueous phase. The base may in particular be an inorganic base, more in particular an alkali-metal hydroxide, such as KOH or NaOH. It is contemplated that such hydroxide or another salt may contribute positively to the dispersibility of the organic phase in the aqueous phase. Further, the use of an alkali-metal hydroxide, has been found to have a positive effect on the efficacy of removing impurity. In particular the hydroxide may react with the impurity, to form a compound that has a higher affinity for the aqueous phase.

If present, the total concentration of bases, in particular one or more alkali-metal hydroxides, usually is at least 0.5 wt. %, in particular at least 1.0 wt. %. The total concentration of bases, in particular one or more alkali-metal hydroxides, is usually 2 wt. % or less, based on the total weight of the aqueous phase.

In a specific embodiment, the flow of the organic phase that is led into an extraction unit wherein the treatment with aqueous phase takes place is regulated by including a provision for recycling organic phase that has been subjected to the extraction into the extraction unit, which provision comprises a regulator for adjusting the recycled flow. This provision can be used to compensate for fluctuations in the flow of fresh organic phase offered to the extraction unit (from upstream of the process, in particular a stream out of a reaction zone wherein the caprolactam has been produced). In case of a temporary decrease in fresh organic phase the recycled flow can be increased accordingly in order to keep the total flow into the extraction unit essentially constant. This is advantageous in view of maintaining a desirable hold-up. Further this may contribute to reducing the risk of flooding, especially in case a sieve tray type wash column is used.

In a preferred embodiment of the invention, a part of the organic phase comprising caprolactam from which impurity has been extracted is recycled into the extraction process. Thus, in a preferred plant of the invention, the extraction zone is provided with a loop for controllably returning a part of the organic phase comprising caprolactam that has left the wash column into the wash column.

Inversed phase operations in general require a laborious startup procedure in which initially a fill-up of the empty column by the small washing liquid flow (under low flow rate, time consuming) is required and next expelled again when the trays approach their steady state situation. The column of the invention however needs just a minimal fill-up initially by the small phase in order to be able to lock the space between a downcomer pipe and the tray below so that the hydraulic pressure of the incoming organic phase is already able to transport the water phase to the upper trays.

After extraction using an aqueous phase, the organic phase comprising caprolactam may further be treated in a manner known per se. One or more of these steps may e.g. be based on the steps described in more detail in WO 02/070475 or another process known per se.

The invention will now be illustrated by the following example.

EXAMPLE

A glass bodied column fitted with 8 sieve trays was used to wash an organic phase (caprolactam in benzene) stream drawn off from a caprolactam plant. The unwashed stream contained—on average—110 ppm ammonium sulphate (determined by ion exchange chromatography) and 21 ppm organic sulphur (as elemental sulphur, measured by element analysis).

The tray distance was 50 cm, the hole diameter 2.5 mm, the number of holes per tray 55, and the diameter of the tray was 20 cm.

Before feeding the organic phase, the column was filled up with water.

At a flow rate of 360 l/hr organic phase from the plant was fed to the bottom part of the column. A wash water flow at a rate of 3.6 l/hr, containing 1.5 wt. % of caustic, was fed on the top tray.

The build up of the organic phase layer below each tray was controlled by the discharge of the water phase, leaving the column from the bottom.

After settling to a steady state profile of layers over the column the washing run was continued for two days.

Every 4 hrs samples of feed and outlet stream of organic phase were taken and analysed. It was found that after washing the average ammonium sulphate concentration was reduced from 110 ppm ammonium sulphate in the organic phase before extraction to less than 1 ppm ammonium sulphate after extraction. The organic sulphur content was reduced from 21 ppm to less than 0.3 ppm (as elemental S, 0.3 ppm being the limit of detection in the used technique).

Comparative Example

An extraction column (10 m filled with 1 inch Raschig packing rings) was used to wash the organic phase originating from the same plant as in the previous Example. This column was equipped with a pulsator mechanism to pulse the liquid inside the column to amplitude of 15 mm and to a frequency of 0.5/s.

The column was filled up with organic phase first. The organic phase feed was positioned below the packing bed, while the wash water feed occurred on top of this bed through a fork type distributor in order to achieve an equal dispersion of this water over the organic phase. The ratio of organic phase to wash water again was 100:1 while the superficial velocity of the benzene lactam phase was kept identical to that of the column in example 1. The wash water had been provided with a 1.5% caustic concentration.

The interface level in the bottom was controlled by the discharge of wash water from the column bottom.

The run was continued for two days to allow for reaching steady state situation and analyzed every 4 hrs.

The average ammonium sulphate concentration in the feed organic phase (prior to extraction) was 102 ppm. In the washed organic phase the average concentration was 55 ppm. The average organic sulphur concentration in the feed organic phase (prior to extraction) was 24 ppm (as elemental S). In the washed organic phase the average concentration was 22 ppm (as elemental S).

The invention claimed is:

1. A process for extracting an impurity from an organic phase comprising caprolactam, comprising extracting the impurity by washing said organic phase as a discontinuous phase with an aqueous phase as a continuous phase, wherein a flow ratio of a flow of the aqueous phase in $m^3$/hr to a flow of the organic phase in $m^3$/hr is 0.05 or less.

2. The process according to claim 1, wherein the flow ratio is 0.001-0.04.

3. The process according to claim 1, wherein the extracting is carried out in an extraction unit in which a volume ratio of a volume of the aqueous phase to a volume of the organic phase is 0.2-0.9.

4. The process according to claim 1, further comprising repeatedly dispersing the organic phase in the aqueous phase to form an organic phase in aqueous phase dispersion and allowing the dispersed organic phase to coalesce.

5. The process according to claim 1, wherein the extracting is carried out in a sieve tray type wash column equipped with downcomers.

6. The process according to claim 1, wherein the aqueous phase comprises one or more alkali-metal hydroxides in a total concentration of 0.5-2 wt. %, based on total weight of the aqueous phase.

7. The process according to claim 1, wherein the organic phase is an organic phase comprising caprolactam prepared in a Beckman rearrangement.

8. The process according to claim 1, wherein the extracting comprises removing one or more sulphur-containing compounds from the organic phase comprising caprolactam in a sieve tray type wash column equipped with downcomers.

9. The process according to claim 2, wherein the flow ratio is 0.002-0.03.

10. The process according to claim 9, wherein the flow ratio is 0.004-0.02.

11. The process according to claim 3, wherein the volume ratio is 0.4-0.75.

12. The process according to claim 11, wherein the volume ratio is 0.45-0.6.

* * * * *